United States Patent [19]

Adams et al.

[11] Patent Number: 4,938,884
[45] Date of Patent: * Jul. 3, 1990

[54] COUPLED PHOSPHORUS-CONTAINING AMIDES

[75] Inventors: Paul Adams, Willoughby; Carmen V. Luciani, Wickliffe, both of Ohio

[73] Assignee: The Lubrizol Corporation, Wickliffe, Ohio

[*] Notice: The portion of the term of this patent subsequent to Jun. 2, 2004 has been disclaimed.

[21] Appl. No.: 300,713

[22] Filed: Jan. 23, 1989

Related U.S. Application Data

[63] Continuation of Ser. No. 730,877, May 3, 1985, abandoned.

[51] Int. Cl.$^5$ ............... C10M 133/16; C10M 137/14
[52] U.S. Cl. .................................................. 252/46.7
[58] Field of Search .................... 252/32.7 R, 32.7 E, 252/46.7

[56] References Cited

U.S. PATENT DOCUMENTS

| | | | |
|---|---|---|---|
| 2,709,156 | 5/1955 | Bishop et al. | 252/46.7 |
| 3,134,801 | 5/1964 | Sehring et al. | 260/461 |
| 3,185,728 | 5/1965 | Schallenberg et al. | 260/501 |
| 3,933,659 | 1/1976 | Lyle et al. | 252/42.7 |
| 4,032,461 | 6/1977 | Hoke | 252/46.7 |
| 4,058,605 | 11/1977 | Cassar | 424/212 |
| 4,073,896 | 2/1978 | Cassar | 424/205 |
| 4,175,043 | 11/1979 | Horodysky | 252/32.7 |
| 4,208,357 | 6/1980 | Hoke | 260/978 |
| 4,212,753 | 7/1980 | Horodysky | 252/46.7 |
| 4,263,150 | 4/1981 | Clason et al. | 252/32.7 R |
| 4,282,171 | 8/1981 | Hoke | 260/928 |
| 4,466,895 | 8/1984 | Schroeck | 252/32.7 E |
| 4,670,169 | 6/1987 | Adams et al. | 252/46.7 |

FOREIGN PATENT DOCUMENTS 819998 7/1949 Fed. Rep. of Germany.

OTHER PUBLICATIONS

German Patent (DDR) 88,534 (Abstract only).
Wolf et al. Dutsche Lebensmittel-Rundschau, vol. 64 (6), pp. 171–177, 1968.

Primary Examiner—William R. Dixon, Jr.
Assistant Examiner—McAvoy
Attorney, Agent, or Firm—Robert A. Franks; Frederick D. Hunter; Forrest L. Collins

[57] ABSTRACT

Coupled amides useful as lubricating additives such as load carrying agents and/or extreme pressure agents have the formula

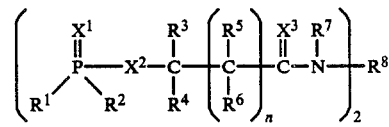

wherein $X^1$, $X^2$, and $X^3$, independently, is O or S;
wherein $R^1$ and $R^2$, independently, is a hydrocarbyl, a hydro-carbyl-based oxy, or a hydrocarbyl-based thio, having from 1 to about 34 carbon atoms;
wherein $R^3$, $R^4$, $R^5$ and $R^6$, independently, is hydrogen, or an alkyl having from 1 to about 22 carbon atoms, a cycloalkyl having from about 4 to about 22 carbon atoms, or an aromatic, an alkyl-substituted aromatic or an aromatic substituted alkyl having from 6 to about 34 carbon atoms;
wherein n is 0 or 1;
wherein $R^7$ is hydrogen or an alkyl having 1 to 22 carbon atoms; and
wherein $R^8$ is an alkylene having from 1 to 12 carbon atoms, phenylene, or an alkyl-substituted phenyl having from 7 to 12 atoms, are useful as lubricant additives such as load carrying agents and/or extreme pressure agents.

20 Claims, No Drawings

COUPLED PHOSPHORUS-CONTAINING AMIDES

This is a continuation of co-pending application Ser. No. 06/730,877 filed on May 3, 1985, now abandoned.

BACKGROUND OF THE INVENTION

The present invention relates to coupled amides which can be employed in the lubrication of at least internal combustion engines, hydraulic equipment, and the like. The coupled amides can be prepared by the reaction of acids such as dialkyl and/or diaryl phosphorodithioic acids reacted with unsaturated hydrocarbyl acrylamides and subsequently coupled.

U.S. Pat. No. 2,709,156 relates to addition products prepared by reacting amides, such as acrylamide, with esterified dithiophosphoric acids.

U.S. Pat. No. 3,134,801 relates to a process for the preparation of O,O-dialkyl-dithiophosphoryl-fatty acid compounds and pesticidal compositions containing the same.

German Patent 819,998 relates to a method of producing esters of phosphoric acid or thiophosphoric acid containing a carboxylic acid amide group.

U.S. Pat. No. 3,185,728 to Schallenberg relates to amine salts of hydrocarbon thiophosphonic acids.

An article by Wolf and Heidenreich, Deutshe Lebensmittel Rundschau, Vol. 64, No. 6, pages 171-177 (1968) relates to the synthesis of organic phosphorous compounds with insecticidal and acaricidal activity such as N,N′-methylenebis(O,O-dialkylphosphorylmercaptoacylamine) wherein the dialkyl phosphoryl groups are usually methyl, ethyl or propyl.

Chem. Abstract Article No. 113832f, Vol. 77, page 401, 1972 relates to acaricidal thiol- and dithiophosphates.

U.S. Pat. No. 4,032,461 to Hoke relates to phosphorous and sulfur containing amides and thioamides as lubricating oil additives and lubricating oil compositions containing the same.

U.S. Pat. No. 4,208,357 to Hoke relates to a process for preparing phosphorous and sulfur containing amides and thioamides.

U.S. Pat. No. 4,282,171 to Hoke also relates to phosphorous and sulfur containing amides and thioamides.

U.S. Pat. No. 4,073,896 to Cassar relates to insecticidal compositions made from dimethylmuconic acid.

U.S. Pat. No. 4,058,605 to Cassar also relates to insecticides from dimethylmuconic acid.

SUMMARY OF THE INVENTION

Accordingly, it is an aspect of the present invention to provide coupled phosphorous containing amide compounds.

It is a further aspect of the present invention to provide coupled phosphorous containing amide compounds, as above, wherein said phosphorous atom has hydrocarbyl, hydrocarbyl-based oxy or hydrocarbyl-based thio substituents.

It is a further aspect of the present invention to provide coupled phosphorous containing amide compounds, as above, wherein the hydrocarbyl portion of the phosphorous substituent is an alkyl, an aromatic such as an alkyl substituted aromatic, or mixtures thereof.

These and other aspects of the present invention will become apparent from the attached specification which fully describes the present invention.

In general, a compound having the formula

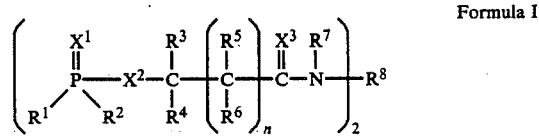

Formula I wherein $X^1$, $X^2$, and $X^3$, independently, is O or S;

wherein $R^1$ and $R^2$, independently, is a hydrocarbyl, a hydrocarbyl-based oxy, or a hydrocarbyl-basaed thio, having from 4 to about 34 carbon atoms;

wherein $R^3$, $R^4$, $R^5$ and $R^6$, independently, is hydrogen, or an alkyl having from 1 to about 22 carbon atoms, a cycloalkyl having from about 4 to about 22 carbon atoms, or an aromatic, an alkyl-substituted aromatic or an aromatic substituted alkyl having from 6 to about 34 carbon atoms;

wherein n is 0 or 1;

wherein $R^7$ is hydrogen or an alkyl having from 1 to 22 carbon atoms; and wherein $R^8$ is an alkylene having from 1 to 12 carbon atoms, phenylene, or an alkyl-substituted phenylene having from 7 to 12 carbon atoms.

DESCRIPTION OF THE PREFERRED EMBODIMENTS

According to the present invention, coupled phosphorous containing amides are described which are useful as load carrying agents, extreme pressure agents, and generally as additives in lubricating compositions.

The compounds of the present invention have the following formula

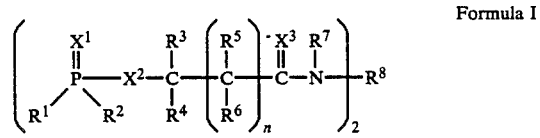

Formula I

Considering $X^1$ and $X^2$, it independently is oxygen or sulphur and preferably is sulfur whereas $X^3$ is O or S and preferably O. $R^1$ and $R^2$ each independently is a hydrocarbyl, a hydrocarbyl-based thio or preferably a hydrocarbyl-based oxy group. The hydrocarbyl portion of $R^1$ and $R^2$ generally contains from 1 to about 34 carbon atoms. The hydrocarbyl portion of $R^1$ and $R^2$ independently can be alkyl or aromatic. Although the hydrocarbyl portion of both $R^1$ and $R^2$ can be the same type of hydrocarbyl group, that is both alkyl or both aromatic, often one such group can be alkyl and the remaining group can be aromatic. It is also within the scope of the present invention to utilize a plurality of different Formula I compounds which are made from a mixture of two or more different reactants each containing an alkyl hydrocarbyl group as well as an aromatic hydrocarbyl ($R^1$ and $R^2$) group therein. Thus, a statistical mixture of compounds of Formula I will be obtained.

The term "hydrocarbyl substituent" or "hydrocarbyl group" is meant throughout this entire specification as well as the claims herein to denote a group having a carbon atom directly attached to the remainder of the molecule and having predominantly hydrocarbon character within the context of this invention. Such groups include the following:

(1) Hydrocarbon groups, that is, aliphatic (e.g., alkyl or alkenyl), alicyclic (e.g., cycloalkyl or cycloalkenyl), aromatic, aliphatic- and alicyclic-substituted aromatic, aromatic-substituted aliphatic and alicyclic groups, and the like, as well as cyclic groups wherein the ring is completed through another portion of the molecule (that is, the two indicated substituents may together form a cyclic group). Such groups are known to those skilled in the art; examples include methyl, ethyl, butyl, hexyl, octyl, decyl, dodecyl, tetradecyl, octadecyl, eicosyl, cyclohexyl, phenyl and naphthyl (all isomers being included).

(2) Substituted hydrocarbon groups, that is, groups containing non-hydrocarbon substituents. Those skilled in the art will be aware of suitable substituents (e.g., halo, hydroxy, alkoxy, carbalkoxy, nitro, alkylsulfoxy).

(3) Hetero groups; that is, groups which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

When the hydrocarbyl group of $R^1$ or $R^2$ is an alkyl, it has from 1 or 4 to about 25 carbon atoms, desirably from 5 to 18 carbon atoms and preferably from 6 to 12 carbon atoms. Examples of such group include methyl, ethyl, propyl, butyl, pentyl, hexyl, heptyl, octyl, nonyl, decyl, dodecyl, tetradecyl, octadecyl, behenyl, and the like, including all isomers thereof. Should the $R^1$ or $R^2$ hydrocarbyl be an aromatic, it can be phenyl or naphthyl. Oftentime it will have an alkyl substituent thereon. Thus, the alkyl substituted aromatic can have an alkyl substituent containing from 0, that is phenyl, to about 28 carbon atoms, and preferably from about 0 or 7 to about 12 carbon atoms. Whenever a blend of the compounds of Formula I is utilized containing significant or effective amounts of alkyl type $R^1$ or $R^2$ substituents, the aromatic substituent can contain preferably from about 0 to about 12 carbon atoms in the alkyl group thereof, that is, the alkyl substituted aromatic. This is because although the solubility of phenyl or low alkyl substituted aromatics may be somewhat low, the overall solubility in a lubricant composition is generally increased to a desirable level through the utilization of the $R^1$ and $R^2$ hydrocarbyl portions which are alkyl and/or through the use of $R^7$ and/or $R^8$ groups which have a large number of carbon atoms therein.

Considering now the alkyl substituted aromatic group, the aromatic preferably is phenyl while the alkyl can be the same as set forth hereinabove. Specific examples of such alkyl groups on the aromatic nucleus include methyl, ethyl, propyl, butyl, pentyl, heptyl, octyl, decyl, behenyl, and the like including isomers thereof.

Accordingly, specific examples of mixed hydrocarbyl ($R^1$ and $R^2$) portions or substituents include tolyl and octyl, tolyl and hexyl, isobutylphenyl and amyl, phenyl and isooctyl, and the like. Mixed hydrocarbyl ($R^1$ and $R^2$) substituents are also assured when cresylic acids are utilized to form the phosphorus portion of the Formula I compound. The sources, type and variety of cresylic acids are known to those skilled in the art.

When $X^1$ and $X^2$ is sulphur and especially when $X^2$ is sulphur, the alkyl hydrocarbyl substituent ($R^1$ or $R^2$) contains 4 or more carbon atoms. However, when $X^1$ or $X^2$ is oxygen and especially when $X^2$ is oxygen, the alkyl hydrocarbyl substituent ($R^1$ or $R^2$) is 5 or more carbon atoms.

Considering $R^3$, $R^4$, $R^5$ and $R^6$, each independently can be hydrogen or a saturated hydrocarbyl having up to 22 carbon atoms. The saturated hydrocarbyl group can be an alkyl having from 1 to 22 carbon atoms, a cycloalkyl having from 4 to 22 carbon atoms, or an aromatic, an aromatic substituted alkyl or an alkyl substituted aromatic having from 6 to about 34 carbon atoms. Preferably, $R^3$, $R^4$, $R^5$, and $R^6$ is hydrogen or methyl with hydrogen being highly preferred. Examples of specific $R^3$, $R^4$, $R^5$, and $R^6$ alkyl groups include methyl, ethyl, propyl, butyl, pentyl, hexyl, heptyl, octyl, nonyl, decyl, dodecyl, tetradecyl, etc., as well as isomers thereof whereas examples of specific aromatic groups include phenyl, tolyl, naphthyl, heptylphenyl, nonylphenyl, dodecylphenyl, wax substituted phenyl, and the like. With regard to the $R^5$—C—$R^6$ group, n can be 0 or 1. Preferably n is 1.

Considering now the amide portion of the molecule, $R^7$ is hydrogen or an alkyl having from 1 to 22 carbon atoms with hydrogen being highly preferred. Examples of specific alkyl groups include methyl, ethyl, propyl, butyl, and so forth including the various isomers thereof.

The coupling group, that is $R^8$, is an alkylene having from 1 to 8 carbon atoms, desirably from 1 to 3 carbon atoms, with 1 carbon atom, that is methylene, being preferred. $R^8$ can also be phenylene, or an alkyl substituted phenylene having from 7 to 12 carbon atoms. Thus, in addition to methylene, $R^8$ can be ethylene, propylene, butylene, pentylene, and so forth, as well as methyl substituted phenylene, ethyl substituted phenylene, propyl substituted phenylene, and so forth.

The products set forth in Formula I can be made by various alternative routes. A preferred route involves the reaction of (A) an acid having the formula

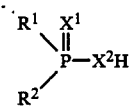

Formula A with (B) an acrylamide type compound having the formula

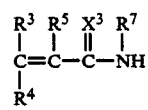

Formula B wherein the various R and the various X groups are as set forth above. That is, with regard to the acid, $X^1$ and $X^2$ are independently oxygen or sulphur with sulphur being preferred. $X^3$ is also oxygen or sulfur but oxygen is preferred. $R^1$ and $R^2$ are independently a hydrocarbyl, a hydrocarbyl-based oxy, or a hydrocarbyl-based thio with the hydrocarbyl-based oxy being preferred. Accordingly, the preferred type of (A) compound is a phosphorodithioic acid wherein the hydrocarbyl groups are both alkyl, both aromatic, or one of each as noted hereinabove. Similarly, $R^3$, $R^4$ and $R^5$ are the same as set forth above with hydrogen or methyl being preferred. $R^7$ can be an alkyl having from 1 to 22 carbon atoms with hydrogen being preferred. The phosphoryldithioic acids (Formula A wherein $X^1$ and $X^2$ are sulfur) of the present invention can be made according to any conventional method as well known to the art. Generally, an alcohol, e.g. alkyl alcohol, aromatic alcohol, or both, is reacted with a phosphorus sulfide such as $P_2S_5$. A suitable reaction route is set forth in U.S. Pat. No. 3,361,668 hereby fully incorporated by reference. Examples of the (B) type reactant include acrylamide, methacrylamide wherein $R^5$ is methyl, and crotonamide.

The reaction between the (A) acid and the (B) amide compound is exothermic and hence only slight heat need be applied thereto. The reaction conveniently can be carried out in an inert atmosphere such as nitrogen as from about 25° to about 100° C. with from about 70° to about 90° being preferred. The reaction can be carried out in the presence or absence of a solvent. Desirably, the reaction takes place in a solvent medium which typically is a hydrocarbon solvent such as toluene, xylene, hexane, heptane, kerosene, fuel oil, an oil of a lubricating viscosity, and the like or a chlorohydrocarbon such as chloroform, carbon tetrachloride, and the like, or an alcohol such as methanol, ethanol, propanol, butanol, 2-ethylhexanol, and the like. The solvent, in addition to acting as such, imparts favorable processing characteristics such as controlling the exothermic reaction as well as preventing unwanted side reactions. The reaction time, while dependent upon temperature, is usually short as less than one or two hours.

The reaction of an acid according to Formula A with an acrylamide type compound of Formula B yields a compound having the following formula

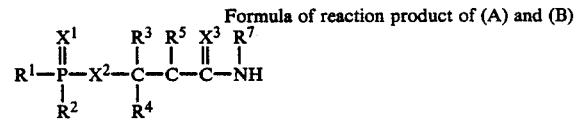

Formula of reaction product of (A) and (B)

Although this reaction product is an intermediate, it also can serve as an end product for use as an additive in a lubricating composition where it functions as a load carrying agent, an extreme pressure anti-wear agent, a corrosion inhibitor, and the like.

After the reaction product of (A) and (B) is formed, it is reacted with an (C) aldehyde or ketone of the following formula

Formula C $R^9$ and $R^{10}$ independently can be hydrogen, an alkyl having from 1 to 12 carbon atoms, phenyl, or an alkyl substituted phenyl having from 7 to 12 carbon atoms. Desirably compound (C) is an aldehyde, i.e. $R^{10}$ is H, having a total of 1 to 3 carbon atoms therein with 1 carbon atom, that is formaldehyde, being highly preferred.

The coupling reaction desirably takes place in the presence of strong mineral or organic acids such as HCl, $H_2SO_4$, $H_3PO_4$, $CH_3SO_3H$, p-toluenesulfonic acid, and the like. The amount of the acid catalyst is generally from about 0.3 to about 1.5 percent by weight, desirably from about 0.8 to about 1.2 percent and preferably from about 0.9 to about 1.1 precent by weight based upon the weight of the total product formed. Although lesser amounts of catalyst can be utilized, the reaction is generally slower and a smaller fraction of the desired product is formed. The reaction with Formula C initially takes place at a temperature of from about 80° C. to about 120° C. and desirably from about 80° C. to about 100° C. in an inert atmosphere. The final reaction temperature is generally higher as from about 100° to about 150° C. and desirably from about 125° to about 135° C.

The amount of reactants (A) and (B) desirably is a 1:1 equivalent weight ratio although greater or lesser amounts can be utilized. A 1:1 equivalent weight ratio of the two reactants is desirable in that otherwise a higher acid number is obtained that desired or else one of the reactants is literally wasted. The amount of reaction product formed and reacted with coupling agent (C) is from about 0.3 to about 3.0 weight equivalents utilized per weight equivalent of said (C) aldehyde or ketone compound with a 1 to 1 equivalent ratio being preferred.

An alternate, although somewhat less desired, method of preparing the compounds of the present invention relates to reacting an (A) acid having the formula

Formula A with (D) a compound having the formula

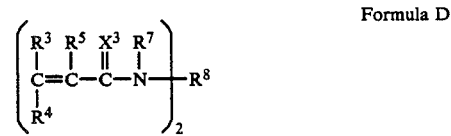

Formula D

The (A) acid is the same as set forth above with regard to the preceding reaction product and hence $X^1$ and $X^2$ can be oxygen or sulphur with sulphur being preferred. While $X^3$ can also be oxygen or sulfur, oxygen is preferred. Similarly, $R^1$ and $R^2$ are the same as set forth above and hence will not be repeated. As previously noted, $R^1$ and $R^2$ can both be an alkyl having from 1 or 4 to 25 carbon atoms or can both be an alkyl-substituted aromatic wherein the alkyl substituent has from 0 to 28 carbon atoms. Moreover, one of the $R^1$ and $R^2$ groups can be an alkyl with the remaining group being an alkyl substituted aromatic. Additionally, more than one acid having the above (A) formulation can be utilized having $R^1$ and $R^2$ substituents therein as set forth in the immediately preceding sentence thereby ensuring that a statistical mixture of the various alkyl and the various alkyl-substituted aromatic groups will exist.

Considering the (D) compound, it is somewhat similar to compound formula (B) set forth hereinabove except that it is coupled by an $R^8$ group. Accordingly, the definition of $R^3$, $R^4$, $R^5$, and $R^7$ is the same as set forth hereinabove with regard to compound (B) and hence will not be repeated but rather is fully hereby incorporated by reference. Thus, by way of summary, the various $R^3$, $R^4$, $R^5$ and $R^7$ groups are essentially saturated hydrocarbyls and preferably are either methyl or hydrogen. Considering $R^8$, it is a hydrocarbylene as discussed above with regard to Formula I. Accordingly, it is an alkylene having from 1 to 8 carbon atoms, desirably from 1 to 3 carbon atoms with methylene being highly preferred. $R^8$ can also be phenylene or an alkyl substituted phenylene having from 7 to 12 carbon atoms.

As with the reaction between acid (A) and compound (B), the reaction between acid (A) and compound (D) is also exothermic and thus requires only a slight amount of heat. Essentially the reaction of compound (D) with the (A) acid is very similar to the reaction of compound (B) and acid (A). Accordingly, the present reaction is carried out desirably in an inert atmosphere at a temperature from about 25° to about 100° with from about 70° to about 90° being preferred. The reaction time is generally short, for example on the order of less than an hour or two. Once again, hydrocarbon solvents such as toluene, xylene, hexane, heptane, kerosene, fuel oil, an oil of a lubricating viscosity, and the like or chlorinated hydrocarbon such as chloroform, carbon tetrachloride, and the like, or an alcohol such as methanol, ethanol, propanol, butanol, 2-ethylhexanol, and the like, are utilized. Once the product has been formed, the various solvents can be removed by stripping under a vacuum and the like.

Yet another alternative method of preparing compounds according to the present invention and especially the coupled compounds set forth hereinabove containing a $R^6$ group is via a displacement reaction. In this reaction, a metal salt of the (A) acid, that is a metal salt according to Formula E

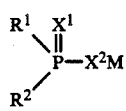

Formula E is reacted with a compound of Formula F

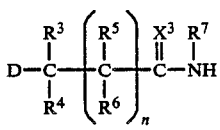

Formula F $X^1$, $X^2$, $X^3$, $R^1$, $R^2$, $R^3$, $R^4$, $R^5$, $R^6$, $R^7$, and n are the same as set forth above and accordingly the description thereof is hereby fully incorporated. M is an alkaline metal such as sodium, potassium or the like, or an alkaline earth metal such as manganese, calcium or the like, or hydrogen, with sodium and potassium being preferred. Considering D, it is a displaceable halogen or carbon group well known to the art such as Cl, Br, I, tosyl, mesyl, and the like. The reaction between the compounds of Formulas E and F proceeds in a manner very similar to that set forth above with regard to making the reaction product between compound A and compound B. Accordingly, the description with regard thereto will not be repeated. Briefly, the reaction is carried out at a temperature of about 10° C. to about 200° C. with from about 50° C. to about 150° C. being preferred. Naturally an inert atmosphere is utilized such as nitrogen. Although not required, the reaction can take place in a solvent medium. The solvent also renders byproduct salts, e.g. KCl, NaCl, NaBr, KBr, etc. which are insoluble in the reaction medium and easily removed by filtration. The amount of Formula E and F compounds are generally an equivalent amount. The formed product has the following formula

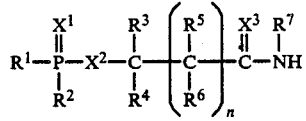

Formula II

The compound of Formula II is then coupled as described hereinabove.

As briefly discussed above, the compounds of the present invention are particularly useful as additives for lubricating compositions. The compounds of the present invention are particularly useful as additives for lubrication where they function primarily as load carrying agents, high or extreme pressure anti-wear agents, oxidation inhibitors, corrosion inhibitors, and the like. Lubricating compositions containing the compounds of the present invention as additives comprise a major proportion of a lubricating oil and a minor portion of said compound sufficient to improve the load carrying ability, anti-wear ability, oxidation inhibitor or corrosion inhibiting properties of the composition. In general, the compounds are used in lubricants in an amount of from about 0.01 to about 5 percent by weight and desirably from about 0.1 to about 1 percent by weight based upon the total weight of the lubricating composition. Additionally, the compounds of the present invention can be utilized in a concentration form or a lubricant concentrate in an amount of from about 0.5 to about 50 percent by weight and more desirably from about 1 to about 25 percent by weight based upon the total weight of the concentrate package. In addition to the compounds of the present invention, the concentrate package can contain one or more compounds such as antiwear agents, load carrying agents, corrosion inhibitors, oxidation inhibitors, demulsifiers, foam inhibitors, VI improvers, pour point depressants, detergents, dispersants, and the like. The compounds of the present invention can also be used as insecticides or pesticides.

The following examples illustrate the preparation of the compounds of the present invention. All parts and percentages are by weight unless otherwise indicated.

EXAMPLE 1

To a mixture of 1775 parts (4.26 equivalents) of di-O-isooctyl phosphorodithioic acid and 980 parts of toluene under a nitrogen atmosphere are added 302 parts (4.26 equivalents) of acrylamide. The reaction mixture exotherms to about 56° C. and 77 parts (2.33 equivalents) of paraformaldehyde and 215 parts (0.11 equivalent) of p-toluenesulfonic acid hydrate are added. Heating is continued at reflux (92°-127° C.) while removing 48 parts of water. Upon cooling the mixture to 100° C., 9.2 parts (0.11 equivalent) of sodium bicarbonate is added and cooling continued to about 30° C. A vacuum is applied (15 mm. Hg) and toluene solvent removed while raising the temperature to 110° C. The residue is filtered through a filter aid and the filtrate is the desired product. The product contains 6.86% P (6.74% theory).

EXAMPLE 2

To a mixture of 1494 parts (3.79 equivalents) of di-O-isooctyl phosphorodithioic acid and 800 parts of toluene under a nitrogen atmosphere are added 537 parts (3.79 equivalents) of 50% aqueous acrylamide solution over a period of one hour. The reaction mixture exotherms to about 53° C. and 64 parts (1.93 equivalents) of paraformaldehyde and 18 parts (0.095 equivalent) of p-toluenesulfonic acid hydrate are added. Heating is continued at reflux (91°-126° C.) for 4 hours while collecting 305 parts of water. The mixture is cooled to about 90° C. and 7.6 parts (0.095 equivalent) of 50% aqueous sodium hydroxide solution are added. Cooling is continued to about 30° C. and a vacuum is applied (15 mm. Hg). Toluene solvent is removed while raising the temperature to 110° C. The residue is filtered through a filter aid and the filtrate is the desired product. The product contains 6.90% P (6.75% theory) and 2.92% N (2.97% theory).

EXAMPLE 3

To a mixture of 984 parts (1.30 equivalents) of di-O-p-dodecylphenyl phosphorodithioic acid and 575 parts of toluene under a nitrogen atmosphere are added 100 parts (0.65 equivalent) of methylenebisacrylamide. The reaction mixture exotherms to about 40° C. and is heated at 80°-85° C. for 2 hours. After cooling the mixture to 30° C., a vacuum (15 mm. Hg) is applied and toluene solvent is removed while raising the temperature to 100° C. The residue is filtered through a filter aid and the filtrate is the desired product. The product contains 4.09% P (4.31% theory).

EXAMPLE 4

A reaction vessel is charged with 820 parts of toluene and 930 parts (2.32 equivalents) of a di-O-alkyl phosphorodithioic acid prepared from a mixture of 20 mole % isobutyl alcohol and 80 mole % 2-ethylhexyl alcohol. To this mixture under a nitrogen atmosphere are added 178.6 parts (1.16 equivalents) of methylenebisacrylamide. The mixture exotherms to about 65° C. and is heated at about 80°-85° C. for 2 hours. Upon cooling to 50° C., a vacuum (30 mm. Hg) is applied. Toluene solvent is removed while raising the temperature to 115° C. The residue is filtered through a filter aid and the filtrate is the desired product. The product contains 7.30% P (7.28% theory).

EXAMPLE 5

To a mixture of 305 parts of toluene and 611 parts (1.82 equivalents) of a di-O-substituted phosophorodithioric acid prepared from a mixture of 20 mole % phenol and 80 mole % i-octyl alcohol, are added 258 parts (1.82 equivalents) of a 50% aqueous acrylamide solution over a 20 minute period under a nitrogen atmosphere. After an initial exotherm to 60° C., 32.1 parts (0.97 equivalents) of paraformaldehyde and 7.3 parts (0.038 equivalent) of p-toluenesulfonic acid hydrate are added. The mixture is heated at reflux (91°-127° C.) for 2 hours while removing 131 parts of water. The mixture is cooled to 80° C. and 3.1 parts (0.038 equivalent) of 50% aqueous sodium hydroxide solution is added. Cooling is continued to 50° C. and a vacuum (30 mm Hg) is applied. Toluene solvent is removed while raising the temperature to 110° C. The residue is filtered through a filter aid and the filtrate is the desired product. The product contains 7.09% P (7.42% theory).

EXAMPLE 6

To 1017 parts (3.0 equivalents) of di-O-methyl-2-pentyl phosphorodithioic acid under nitrogen is added 213 parts (3.0 equivalents) of acrylamide. The reaction exotherms to 65° C. and held for one to three hours at 65°-75° C. The product is filtered through filter aid and filtrate is product. The product contains 7.65% P (7.82 theory), 3.51% N (3.50 theory), and 16.05% S (16.06% theory).

EXAMPLE 7

To 614 parts (1.5 equivalents) of di-O-isooctyl phosphorodithioic acid under nitrogen is added 213 parts (1.5 equivalents) of a 50% aqueous acrylamide solution. The reaction exotherms to 65° C. and held for two hours at 70° C. A vacuum is applied (20 mm Hg) while raising temperature to 90° C. The residue is filtered through filter aid. Filtrate is the desired product. The product contains 6.67% P (6.60 theory), 2.94% N (2.97 theory), and 14.50% S (13.60 theory).

As previously noted, the compositions of the present invention are useful as additives for lubricants and functional fluids. They can be employed in a variety of lubricants based on diverse oils lubricating viscosity, including natural and synthetic lubricating oils and mixtures thereof.

These lubricating compostions containing the subject additive concentrates are effective as crankcase lubricating oils for spark-ignited and compression-ignited internal combustion engines, including automobile and truck engines, two-cycle engines, aviation piston engines, marine, railroad and low-load diesel engines, and the like. Also, automatic transmission fluids, transaxle lubricants, gear lubricants, metal-working lubricants, hydraulic fluids, and other lubricating oil and grease compositions can benefit from the incorporation of the subject additive concentrates.

Natural oils include animal oils and vegetable oils (e.g., castor oil, lard oil) as well as mineral lubricating oils such as liquid petroleum oils and solvent-treated or acid-treated mineral lubricating oils of the paraffinic, naphthenic or mixed paraffinic-naphthenic types. Oils of lubricating viscosity derived from coal or shale are also useful. Synthetic lubricating oils include hydrocarbon oils and halosubstituted hydrocarbon oils such as polymerized and interpolymerized olefins (e.g., polybutylenes, polypropylenes, propyleneisobutylene copolymers, chlorinated polybutylenes, etc.); poly(1-hexenes), poly(1-octenes), poly(1-decenes), etc. and mixtures thereof; tetradecylbenzenes, dinonylbenzenes, di-(2-ethylhexyl)-benzenes, etc.); polyphenyls (e.g., biphenyls, terphenyls, alkylated polyphenyls, etc.); alkylated diphenyl ethers and alkylated diphenylsulfides and the derivatives, analogs and homologs thereof and the like.

Alkylene oxide polymers and interpolymers and derivatives thereof where the terminal hydroxyl groups have been modified by esterification, etherification, etc., constitute another class of known synthetic lubricating oils that can be used. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of about 1000, diphenyl ether of polyethylene glycol having a molecular weight of about 500–1000, diethyl ether of polypropylene glycol having a molecular weight of about 1000–1500, etc.) or mono- and polycarboxylic esters thereof, for example, the acetic acid esters, mixed $C_3$–$C_8$ fatty acid ester, or the $C_{13}$Oxo acid diester of tetraehylene glycol.

Another suitable class of synthetic lubricating oils that can be used comprises the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_5$ to $C_{12}$ monocarboxylic acids and polyols and plyol ethers such as neopentyl glycol, trimethylol propane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl)silicate, tetra-(4-methylhexyl)silicate, tetra-(p-tert-butylphenyl)silicate, hexyl-(4-methyl-2-pentoxy)disiloxane, poly(methyl)siloxanes, poly(methylphenyl)siloxanes, etc.). Other synthetic lubricating oils include liquid esters of phosphorus-containing acids (e.g., tricresyl phosphate, trioctyl phsophate, diethyl ester of decane phosphonic acid, etc.), polymeric tetrahydrofurans and the like.

Unrefined, refined and rerefined oils, either natural or synthetic (as well as mixtures of two or more of any of these) of the type disclosed hereinabove can be used in the concentrates of the present invention. Unrefined oils are those obtained directly from a natural or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those skilled in the art such as solvent extraction, secondary distillation, acid or base extraction, filtration, percolation, etc. Rerefined oils are obtained by processes similar to those used to obtain refined oils applied to refined oils which have been already used in service. Such refined oils are also known as reclaimed or reprocessed oils and often are additionally processed by techniques directed to removal of spent additives, oil breakdown products, and combustion products.

Generally the lubricants of the present invention contain an amount of one or more of the compounds of the present invention sufficient to provide them with improved antioxidant, anti-wear and/or extreme pressure properties, load carrying properties and the like.

The invention also contemplates the use of other additives in combination with the compounds of the present invention. Such additives include, for example, detergents and dispersants of the ash-producing or ashless type, corrosion- and oxidation-inhibiting agents, pour point depressing agents, extreme pressure agents, antiwear agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature of about 50° C. and filtering the resulting mass. The use of a "promoter" in the neutralization step to aid the incorporation of a large excess of metal likewise is known. Examples of compounds useful as the promotor include phenolic substances such as phenol, naphthol, alkylphenol, thiophenyl, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-beta-naphthylamine, and dodecylamine. A particularly effective method for preparing the base salts comprises mixing an acid with an excess of a basic alkaline earth metal neutralizing agent and at least one alcohol promoter, and carbonating the mixture at an elevated temperature such as 60°-200° C.

Ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the lubricant compositions of this invention. The following are illustrative:

(1) Reaction products of carboxylic acids (or derivatives thereof) containing at least about 34 and preferably at least about 54 carbon atoms with nitrogen containing compounds such as amine, organic hydroxy compounds such as phenols and alcohols, and/or basic inorganic materials. Examples of these "carboxylic dispersants" are described in British Patent 1,306,529 and in many U.S. Pat. Nos. including the following:

| | | |
|---|---|---|
| 3,163,603 | 3,351,552 | 3,541,012 |
| 3,184,474 | 3,381,022 | 3,543,878 |
| 3,215,707 | 3,399,141 | 3,542,680 |
| 3,219,666 | 3,415,750 | 3,567,637 |
| 3,271,310 | 3,433,744 | 3,574,101 |
| 3,272,746 | 3,444,170 | 3,576,743 |
| 3,281,357 | 3,448,048 | 3,630,904 |
| 3,306,908 | 3,448,049 | 3,632,510 |
| 3,311,558 | 3,451,933 | 3,632,511 |
| 3,316,177 | 3,454,607 | 3,697,428 |
| 3,340,281 | 3,467,668 | 3,725,441 |
| 3,341,542 | 3,501,405 | 4,234,435 |
| 3,356,493 | 3,522,179 | Re26.433 |

(2) Reaction products of relatively high molecular weight aliphatic or alicyclic halides with amines, preferably olyalkylene polyamines. These may be characterized as "amine dispersants" and examples thereof are described for example, in the following U.S. Pat. Nos.:

| | |
|---|---|
| 3,275,554 | 3,454,555 |
| 3,438,757 | 3,565,804 |

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. Pat. Nos. are illustrative:

| | | |
|---|---|---|
| 2,459,112 | 3,442,808 | 3,591,598 |
| 2,962,442 | 3,448,047 | 3,600,372 |
| 2,984,550 | 3,454,497 | 3,634,515 |
| 3,036,003 | 3,459,661 | 3,649,229 |
| 3,166,516 | 3,461,172 | 3,697,574 |
| 3,236,770 | 3,493,520 | 3,725,277 |
| 3,355,270 | 3,539,633 | 3,725,480 |
| 3,368,972 | 3,558,743 | 3,726,882 |
| 3,413,347 | 3,586,629 | 3,980,569 |

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos.:

| | | | |
|---|---|---|---|
| 3,036,003 | 3,282,955 | 3,493,520 | 3,639,242 |
| 3,087,936 | 3,312,619 | 3,502,677 | 3,649,229 |
| 3,200,107 | 3,366,569 | 3,513,093 | 3,649,659 |
| 3,216,936 | 3,367,943 | 3,533,945 | 3,658,836 |
| 3,254,025 | 3,373,111 | 3,539,633 | 3,697,574 |
| 3,256,185 | 3,403,102 | 3,573,010 | 3,702,757 |
| 3,278,550 | 3,442,808 | 3,579,450 | 3,703,536 |
| 3,280,234 | 3,455,831 | 3,591,598 | 3,704,308 |
| 3,281,428 | 3,455,832 | 3,600,372 | 3,708,422 |

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. Pat. Nos.:

| | |
|---|---|
| 3,329,658 | 3,666,730 |
| 3,449,250 | 3,687,849 |
| 3,519,565 | 3,702,300 |

The above-noted patents are incorporated by reference herein for their disclosures of ashless dispersants.

Extreme pressure agents and corrosion- and oxidation-inhibiting agents which may be included in the lubricants of the invention are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate, phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)-phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

Many of the above-mentioned auxiliary extreme pressure agents and corrosion-oxidation inhibitors also serve as antiwear agents. Zinc dialkylphosphorodithioates are a well known example.

Pour point depressants are a particularly useful type of additive often included in the lubricating oils described herein. The use of such pour point depressants in oil-based compositions to improve low temperature properties of oil-based compositions is well known in the art. See, for example, page 8 of "Lubricant Additives" by C. V. Smalheer and R. Kennedy Smith (Lezius-Hiles Co. publishers, Cleveland, Ohio, 1967).

Examples of useful pour point depressants are polymethacrylates; polyacrylates; polyacrylamides; condensation products of haloparaffin waxes and aromatic compounds; vinyl carboxylate polymers; and terpolymers of dialkylfumarates, vinyl esters of fatty acids and alkyl vinyl ethers. Pour point depressants useful for the purposes of this invention, techniques for their preparation and their uses are described in U.S. Pat. Nos. 2,387,501; 2,015,748; 2,655,479; 1,815,022; 2,191,498; 2,666,746; 2,721,877; 2,721,878; and 3,250,715 which are hereby incorporated by reference for their relevant disclosures.

Anti-foam agents are used to reduce or prevent the formation of stable foam. Typical anti-foam agents include silicones or organic polymers. Additional anti-foam compositions are described in "Foam Control Agents", by Henty T. Kerner (Noyes Data Corporation, 1976), pages 125-162.

The sulfurized compositions of this invention can be added directly to the lubricant. Preferably, however, they are diluted with a substantially inert, normally liquid organic diluent such as mineral oil, naphtha, benzene, toluene or xylene, to form an additive concentrate. These concentrates usually contain from about 1% to about 50% by weight of the sulfurized compositions of this invention and may contain, in addition, one or more other additives known in the art or described hereinabove. The remainder of the concentrate is the substantially inert normally liquid diluent.

As noted above, the coupled phosphorous containing amide type compounds of the present invention can be added directly to the lubricant in amounts as set forth above. Additionally, they are often diluted with a substantially inert, normally liquid organic diluent such as mineral oil, naphtha, benzene, toluene, xylene, and the like to form an additive concentrate. The concentrates can furthermore contain one or more additives known to the art or described hereinabove. The remainder of the concentrate is a substantially inert normally liquid diluent.

An example of a concentrate is as follows:

| Product of Example 2 | 15% by wt. |
|---|---|
| Zn salt of a phosphorodithioic acid | 50% by wt. |
| Oxidation inhibitor | 20% by wt. |
| Rust inhibitor | 5% by wt. |
| Mineral oil | 10% by wt. |

The concentrate had good solubility with regard to the product of Example 2 therein.

When 1 part by weight of the above concentrate was used in 99 parts by weight of a mineral oil and the resulting solution tested with regard to a F.Z.G. gear test, an improvement from a pass 10 load stage to a pass 12 load stage was noted.

While in accordance with the patent statutes, a best mode and preferred embodiment has been set forth, it is to be understood that various modifications thereof will become apparent to those skilled in the art upon a reading of the specification. Therefore, it is to be understood that the invention disclosed herein is intended to cover such modifications as fall within the scope of the attached claims.

What is claimed is:

1. A lubricating composition comprising: a lubricating oil and an effective amount of a load carrying agent which is a coupled amide compound having the formula

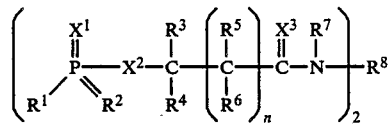

wherein $X^1$, $X^2$ and $X^3$, independently, is O or S;
wherein $R^1$ and $R^2$, independently, is a hydrocarbyl, a hydrocarbyl-based oxy wherein the hydrocarbyl portion is an alkyl having from 6 to 12 carbon atoms, or a hydrocarbyl-based thio, having from 1 to about 34 carbon atoms;
wherein $R^3$, $R^4$, $R^5$ and $R^6$, independently, is hydrogen, or an alkyl having from 1 to about 22 carbon atoms, a cycloalkyl having from about 4 to about 22 carbon atoms, or an aromatic, an alkyl-substituted aromatic or an aromatic substituted alkyl having from 6 to about 34 carbon atoms;
wherein n is 0 or 1;
wherein $R^7$ is hydrogen or an alkyl having from 1 to 22 carbon atoms; and
wherein $R^8$ is an alkylene having from 1 to 12 carbon atoms, phenylene, or an alkyl-substituted phenylene having from 7 to 12 carbon atoms.

2. A lubricating composition according to claim 1, wherein said hydrocarbyl portion of said $R^1$ and $R^2$, independently, is an alkyl having from 6 to 12 carbon atoms or an aromatic which may be substituted with an alkyl substituent containing 1 to about 28 carbon atoms, and wherein $R^3$, $R^4$, $R^5$ and $R^6$, independently, is hydrogen, an alkyl having from 1 to 22 carbon atoms, or an aromatic or alkyl-substituted aromatic having from 6 to 34 carbon atoms.

3. A lubricating composition according to claim 1 wherein $X^1$ and $X^2$ is S, wherein $X^3$ is O, wherein $R^1$ and $R^2$ is an alkyl-substituted aromatic wherein said alkyl substituent has from 7 to 12 carbon atoms, wherein $R^3$, $R^4$, $R^5$ and $R^6$, independently, is hydrogen or methyl; wherein n is 1;
wherein $R^7$ is hydrogen; and
wherein $R^8$ is methylene.

4. The lubricating composition of claim 1, wherein the hydrocarbyl portion of $R^1$ and $R^2$ is each independently an alkyl selected from the group consisting of hexyl, heptyl, octyl, nonyl, decyl, dodecyl, tetradecyl, octadecyl and behenyl.

5. A lubricating composition comprising a major portion of a lubricating oil and a minor portion of a load carrying agent comprising:
the reaction product of (A) an acid having the formula

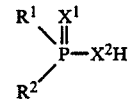

wherein $X^1$ and $X^2$, independently, is O or S;
wherein $R^1$ and $R^2$, independently, is a hydrocarbyl, a hydrocarbyl-based oxy, having from 6 to 12 carbon atoms or a hydrocarbyl-based thio having from 4 to about 34 carbon atoms, and (B) a compound having the formula

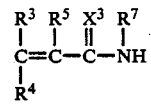

wherein $X^3$ is O or S, wherein $R^3$, $R^4$ and $R^5$, independently, is hydrogen or a saturated hydrocarbyl having from 1 to 34 carbon atoms, wherein $R^7$ is hydrogen or an alkyl having from 1 to 22 carbon atoms, and the subsequent reaction of the product formed thereby with (C) a compound having the formula

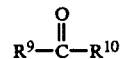

where $R^9$ and $R^{10}$, independently, is hydrogen, an alkyl having from 1 to 12 carbon atoms, phenyl, or an alkyl-substituted phenyl having from 7 to 12 carbon atoms.

6. A lubricating composition according to claim 5, wherein $R^9$ and $R^{10}$, independently, is hydrogen or an alkyl having from 1 to 12 carbon atoms.

7. A lubricating composition according to claim 5, wherein $X^1$ and $X^2$ is S, wherein $X^3$ is O, wherein $R^1$ and $R^2$ is a hydrocarbyl based oxy wherein said hydrocarbyl portion is, independently, an aromatic which may be substituted with an alkyl substituent containing 1 to 12 carbon atoms, and wherein $R^9$ and $R^{10}$, independently, is hydrogen or alkyl having 1 or 2 carbon atoms, and wherein $R^7$ is hydrogen.

8. A lubricating composition according to claim 4, wherein $R^3$, $R^4$ and $R^5$, independently, is hydrogen or methyl.

9. A lubricating composition according to claim 5, wherein $X^1$ and $X^2$ is S, wherein $X^3$ is O, wherein $R^3$, $R^4$ and $R^5$, independently, is hydrogen or methyl, wherein $R^7$ is hydrogen and wherein $R^9$ and $R^{10}$ is hydrogen.

10. The lubricating composition of claim 5, wherein the hydrocarbyl portion of $R^1$ and $R^2$ is each independently an alkyl selected from the group consisting of hexyl, heptyl, octyl, nonyl, decyl, dodecyl, tetradecyl, octadecyl and behenyl.

11. A lubricating composition comprising a major portion of a lubricating oil and a minor portion of a load carrying agent comprising:
the reaction product of (A) an acid having the formula

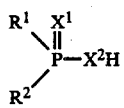

wherein $X^1$ and $X^2$, independently, is O or S;
wherein $R^1$ and $R^2$, independently, is a hydrocarbyl, a hydrocarbyl-based oxy wherein the hydrocarbyl portion is independently an alkyl having from 6 to 12 carbon atoms or an aromatic which may be substituted with an alkyl substituent containing 1 to 12 carbon atoms, or a hydrocarbyl-based thio having from 4 to about 34 carbon atoms, and (D) a compound having the formula

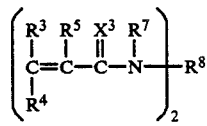

wherein $X^3$ is O or S, wherein $R^3$, $R^4$ and $R^5$, independently, is hydrogen or a saturated hydrocarbyl having from 1 to 34 carbon atoms, wherein $R^7$ is hydrogen or an alkyl having from 1 to 22 carbon atoms, and where $R^8$ is an alkylene having from 1 to 12 carbon atoms, phenylene, or an alkyl-substituted phenylene having from 7 to 12 carbon atoms.

12. A lubricating composition according to claim 11, wherein $R^3$, $R^4$ and $R^5$, independently, is hydrogen, an alkyl having from 1 to 22 carbon atoms, an aromatic or an alkyl-substituted aromatic having from 6 to 34 carbon atoms.

13. A lubricating composition according to claim 12, wherein $R^8$ is an alkylene having from 1 to 12 carbon atoms, wherein $X^1$ and $X^2$ is sulfur, and wherein $X^3$ is oxygen.

14. A lubricating composition according to claim 12, wherein $R^3$, $R^4$ and $R^5$, independently, is hydrogen or methyl.

15. A lubricating composition according to claim 14, wherein the hydrocarbyl portion of $R^1$ and $R^2$, independently, is an alkyl-substituted aromatic wherein said alkyl substituent has from 7 to 12 carbon atoms.

16. The lubricating composition of claim 11, wherein the hydrocarbyl portion of $R^1$ and $R^2$ is each independently an alkyl selected from the group consisting of hexyl, heptyl, octyl, nonyl, decyl, dodecyl, tetradecyl, octadecyl and behenyl.

17. A lubricating composition comprising a major portion of a lubricating oil and a minor portion of a load carrying agent having the formula Formula II

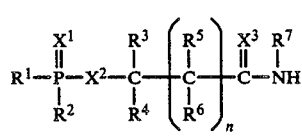

wherein $X^1$ and $X^2$ is S and $X^3$ is O;
wherein $R^1$ and $R^2$, independently, is a hydrocarbyl, a hydrocarbyl-based oxy wherein the hydrocarbyl portion is independently an alkyl having 6 to 12 carbons or an aromatic which may be substituted with an alkyl substituent having 1 to 12 carbon atoms, or a hydrocarbyl-based thio, having from 1 to about 34 carbon atoms;
wherein $R^3$, $R^4$, $R^5$ and $R^6$, independently, is hydrogen, or an alkyl having from about 1 to 22 carbon atoms, a cycloalkyl having from about 4 to 22 carbon atoms, or an aromatic, an alkyl-substituted aromatic or an aromatic-substituted alkyl having from 6 to 34 carbon atoms;
wherein n is 1; and
wherein $R^7$ is hydrogen.

18. A lubricating composition according to claim 17, wherein $R^3$, $R^4$, $R^5$ and $R^6$, independently, is hydrogen, an alkyl having from 1 to 22 carbon atoms, an aromatic or an alkyl substituted aromatic having from 6 to 34 carbon atoms.

19. A lubricating composition according to claim 18, wherein $R^3$, $R^4$, $R^5$ and $R^6$, independently, is hydrogen or methyl;
wherein n is 1; wherein $R^7$ is hydrogen; and wherein $X^1$ and $X^2$ is S, and wherein $X^3$ is O.

20. A lubricating composition according to claim 19, wherein said alkyl portion of $R^1$ and $R^2$ is octyl.

* * * * *